United States Patent

Nessler

(10) Patent No.: US 8,545,494 B2
(45) Date of Patent: Oct. 1, 2013

(54) DEVICE FOR TESTING A NEUTRAL ELECTRODE

(75) Inventor: Norbert Nessler, Innsbruck (AT)

(73) Assignee: Norbert Nessler (AT)

(*) Notice: Subject to any disclaimer, the term of this patent is extended or adjusted under 35 U.S.C. 154(b) by 1786 days.

(21) Appl. No.: 10/528,841

(22) PCT Filed: Sep. 11, 2003

(86) PCT No.: PCT/AT03/00270
§ 371 (c)(1),
(2), (4) Date: Feb. 8, 2006

(87) PCT Pub. No.: WO2004/028387
PCT Pub. Date: Apr. 8, 2004

(65) Prior Publication Data
US 2006/0173250 A1    Aug. 3, 2006

(30) Foreign Application Priority Data
Sep. 24, 2002    (AT) ................. A 1428/2002

(51) Int. Cl.
*A61B 18/16*    (2006.01)
(52) U.S. Cl.
USPC .......................................................... 606/35
(58) Field of Classification Search
USPC ............ 606/34, 35; 703/14; 324/600, 601, 324/691, 692, 701–703
See application file for complete search history.

(56) References Cited

U.S. PATENT DOCUMENTS 9,752,401    6/1988    Bodenstein

FOREIGN PATENT DOCUMENTS

| DE | 154 064 | 11/1980 |
| DE | 262 324 A3 | 11/1988 |
| WO | WO 00/71227 | 11/2000 |

OTHER PUBLICATIONS

Ronald Pethig, Dielectric Properties of Biological Materials: Biophysical and Medical Applications, Oct. 1984, IEEE Transactions on Electrical Insulation, vol. EI-19 No. 5, 453-471.*
Nessler N. et al. The Nuetral Electrode in Electrosurgery, A Risk for the Patient, Jun. 12, 2001, pp. 269-272.
Nessler N. et al. Testing Device for Surgical Grounding Plates, date NA, pp. 2388-2389.
N. Nessler et al. Safety Testing of High Frequency Surgery Nuetral Electrodes (Measuring Instrument for Impedance and Temperatureincreas). Jan. 1993, pp. 5-9.
S. Gabriel et al. The Dielectric Properties of Biological Tissues. Nov. 1, 1996. pp. 2251-2269.

* cited by examiner

Primary Examiner — Ronald Hupczey, Jr.
(74) Attorney, Agent, or Firm — Paul & Paul (57) ABSTRACT

The invention relates to a device for testing a neutral electrode (1) for use in electrosurgery, comprising a measuring surface (25) which is formed by a plurality of measuring electrodes (20), whereon the neutral electrode (1) is applied. Each measuring electrode (20) of the measuring surface (25) is connected to a replacement resistance circuit (70) representing at least one layer of the human skin, which is placed in thermal contact with at least one temperature sensor (90). At least one resistance of the replacement-resistance circuit (70) is formed by means of a blind resistance (54).

19 Claims, 8 Drawing Sheets

PRIOR ART

DEVICE FOR TESTING A NEUTRAL ELECTRODE

This application is a national stage entry of PCT/AT03/00270, filed Sep. 11, 2003, and claims priority to Austrian Patent Document No. A 1428/2002, filed Sep. 24, 2002. The contents of each of these documents are incorporated herein by reference.

FIELD OF THE INVENTION

This invention relates to a device for testing a neutral electrode for use in electrosurgery.

BACKGROUND OF THE INVENTION

Cutting and coagulating tissue by using a high-frequency current is standard practice in electrosurgery. As is shown in the sectional drawing of FIG. 1, in the so-called monopolar technique, the desired surgical effect is achieved by introducing a HF current into a human or animal body 6 via an active electrode 2, which has a relatively small surface and is supported on a handpiece, and returning it to a HF generator 3 via a neutral electrode 1, which has a relatively large surface and is usually applied to the thigh, sometimes to the upper arm or the back. At the same time, the neutral electrode serves for grounding the patient. Modern neutral electrodes are self-adhesive, single-use contact surfaces of various sizes and shapes.

Unlike an active electrode, where quick heating produces the desired surgical effect, the neutral electrode must not heat the patient's skin by more than 6° C. Corresponding tests are specified in the ANSI-AAMI HF18-93 standard (American National Institute, Association for the Advancement of Medical Instrumentation, Electrosurgical Devices, Arlington, USA, 1993). Here, one electrode type is tested with at least five male and five female subjects under a given current load, and the temperature is usually measured by means of a thermo camera. Alternatively, a substitute medium not described in greater detail, which is demonstrably suited for simulating the electrical and thermal properties of the thermally most sensitive subject, may substitute for the subjects.

Investigation in this field, conducted at the University of Innsbruck, Austria (N. Nessler, H. Huter, L. Wang, Testing Device for Surgical grounding plates, 14'" Annual International Conference of the IEEE Engineering in Medicine and Biology Society, Paris, 1992; H. Huter, Entwicklung eines Meßgerätes für thermische und elektrische Gleichmaßigkeit von Neutraletektroden der HF-Chirurgie, thesis at the University of Innsbruck, 1992; N. Nessler, H. Huter, L. Wang, Sicherheitstester für HF-Chirurgie-Neutralelektroden, Biomedizinische Technik Vol. 38, pp. 5-9, 1993), lead to the development of an electronic device (GPTest 11) which simulates the properties of a patient's skin in a first approximation to such an extent that a neutral electrode can be tested under the current load of 700 mA specified by the AAMI HF18 standard for a measuring time of 60 sec. The temperature increase thus generated is measured and results in measuring values comparable with those obtained with a human subject (N. Nessler, Skin Temperature Scan with Flexible Sensor Array, 16th BEMS Meeting, Copenhagen, 1994; N. Nessler, Current Density Distribution in Human Skin under the Grounding Electrode of Electrosurgery, BEMS 17th Annual Meeting, Boston, Mass., 1995).

SUMMARY OF THE INVENTION

The device mentioned above does not, however, simulate the edge effect caused by volume conduction in the skin layers and muscle fibers of the tissue covered by the neutral electrode, which leads to a current concentration and thus to peak temperature values along the periphery of the neutral electrode.

The invention is a device for testing a neutral electrode for use in electrosurgery, comprising a measuring surface which is formed by a plurality of measuring electrodes, whereon the neutral electrode may be applied, wherein each measuring electrode of the measuring surface is connected to an equivalent resistance circuit representing at least one layer of the human skin, i.e., the epidermis, the corium and the hypodermis including fatty tissue, and consisting of at least two resistances, which equivalent resistance circuit is in thermal contact with at least one temperature sensor.

For electronic simulation of skin in the GPTest II device, the test conditions of the AAMI HF-18 standard were used, which include the determination of temperature distribution across the entire surface of the neutral electrode by determining the temperature values in areas of 1 $cm^2$. Here, a measuring surface, usually a measuring circuit board having a gold-plated contact surface of corresponding size, e.g. 10 cm×18 cm, is divided into a plurality of square measuring electrodes 1 $cm^2$ in size, and associated feedthroughs on the back of the measuring circuit board are each connected to ground via an ohmic equivalent resistance of e.g. 1 kohm as average main impedance. Each measuring electrode has a temperature sensor consisting of a transistor in thermal contact with a respective equivalent resistance whose temperature-dependent basic emitter voltage (−2 mV/° C.) results in an electronically analyzable temperature measuring value. If a neutral electrode is applied to the measuring circuit board, which is divided into measuring electrodes electrically insulated from each other, and loaded with a current of 700 mA for 60 s, as is provided by the AAMI HF-18 standard, the temperature distribution caused by the plurality of equivalent resistances connected to the measuring electrodes and the respective basic emitter voltages before and after the heating phase are analyzed by means of an electronic circuit, e.g. in the form of a matrix scan.

Again, this simplified electronic representation of human skin as one resistance value per $cm^2$ against the ground does not simulate the edge effect, which, depending on the constitution and thickness of the skin, leads to different current concentrations along the periphery of the neutral electrode because cross impedance, which is actually existent in skin and parallel to the skin surface, is not simulated. The temperatures measured by means of this arrangement are consequently substantially equal across the entire neutral electrode surface and thus lead to a relatively rough estimation of the thermal load expected for a subject.

Figure 2:
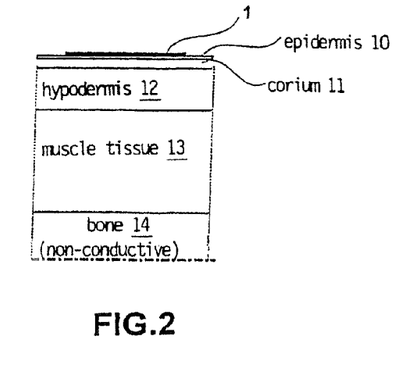
FIG. 2 shows a schematic sectional view of a supposed layer structure.

Current distribution within the body, especially within the thigh, is not accessible in a direct measurement, which is why a model calculation has been conducted at the University of Innsbruck (N. Nessler, "Die Neutralelektrode bei der Elektrochirurgie, ein Risiko für den Patienten?", Österr. Krankenhauszeitung ÖKZ, 12/95, p. 29-34, 1995; N. Nessler, "Current density distribution in Human skin under the Grounding electrode of Electrosurgery", BEMS 17th Annual Meeting Boston, Mass., 1995). In this calculation known as cylinder model, a thigh with different skin and muscle layers was simulated, and local current path, voltage path, and local dissipation power were calculated by means of the finite elements method. FIG. 2 is a schematic sectional view of the supposed layer structure in the patient's body, wherein the neutral electrode 1 is supported on an epidermis layer 10, underneath follow a corium layer 11, a hypodermis layer 12 including fatty tissue, and a muscle layer 13 which is adjacent to a practically non-conductive bone layer 14. Here, the calculated current distribution at the skin surface corresponds to the heating pattern obtained in subjects under the same conditions. This model calculation leads to the expected edge affect, i.e. current concentration at the periphery of the neutral electrode and also a higher load at the part of the neutral electrode periphery closer to the surgical site, which phenomenon is reflected in a directional dependence of the stronger temperature increase in the periphery of the neutral electrode. Because of this directional dependence, tissue situated closer to the surgical site is heated more strongly than tissue situated further away.

For electronic simulation of this model, according to the division defined by the AAMI HF-18 standard, a corresponding number of measuring prism cells may be presumed for the plurality of measuring electrodes 1 $cm^2$ in size, which measuring prism cells are divided into partial prism cells simulating different skin and muscle layers of the patient. Starting from the center of the each partial prism cell, the respective skin or muscle layer is represented by resistances arranged, according to the equivalent circuit of the impedances in the skin layer, in three spatial directions, horizontally in the x and y direction as well as vertically in the z direction (S. Gabriel, R. W. Lau, C. Gabriel, "The dielectric properties of biological tissue"; "II Measurements in the frequency range 10 Hz to 20 GHz", Phys. Medikament. Biol. 41, 2251-2293, 1996). This model requires six resistances per layer, adding up to 24 resistances per 1 $cm^2$ measuring electrode for the epidermis 10, the corium 11, the hypodermis 12 including fatty tissue, and the muscle volume 13 (FIG. 2). With the skin layers shown in FIG. 2, a thigh was modeled and currents as well as corresponding power values were calculated.

Figure 3:
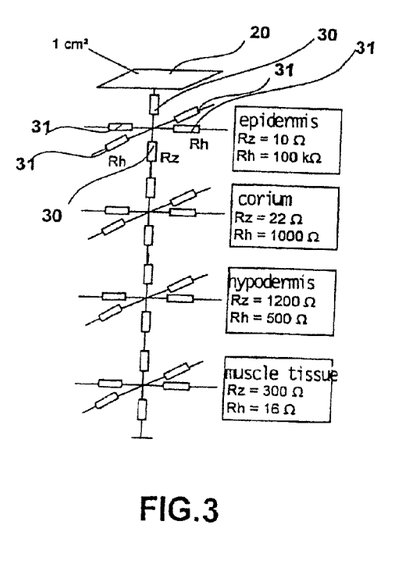
FIG. 3 shows a circuit diagram of an equivalent resistance network for a measuring electrode.

The resulting three-dimensional equivalent resistance network simulates the properties of skin for a HF current including the edge and directional effects. A circuit diagram of the equivalent resistance network for a measuring electrode 20 of the measuring surface is shown in FIG. 3. Each skin layer is represented by four horizontal resistances 31 (Rh) and two vertical resistances 30 (Rz), e.g. epidermis: Rz=10 ohms, Rh=100 kohms, corium: Rz=22 ohms, Rh=1000 ohms, hypodermis: Rz=1200 ohms, Rh=500 ohms, muscle tissue: Rz=300 ohms, Rh=16 ohms. At one terminal, each horizontal resistance 31 is connected to the node of the partial prism cell of a skin layer, and its other terminal is connected to the horizontal resistance 31 of the respective adjacent partial prism cell of the same skin layer. The upper vertical equivalent resistance 30 of the hypodermis layer of each measuring prism cell is at one end directly connected to the measuring electrode 20, while the lower vertical equivalent resistance 30 of the muscle tissue layer is at one end connected to ground. The intermediate vertical equivalent resistances 30 are each connected to the node of a corresponding partial prism cell and the vertical equivalent resistance of the partial prism cell above or below it.

Even if very small components are used, e.g. SMD components, the equivalent resistances 30, 31 cannot be packed sufficiently densely to provide for 24 resistances on 1 $cm^2$ of a circuit board. In order to simplify this model, a plane skin model with the neutral electrode was calculated, wherein it was made sure that the results were substantially the same as in the cylinder model or in measurements with subjects. Because of its low ohmic resistance, in this model, the highly conductive muscle volume with its large cross section was replaced by an equipotential surface, i.e. a surface with an infinite conductivity. A disadvantage of this simplification is that the directional dependence of the neutral electrode's temperature increase is lost, the other skin properties, however, are maintained in the model. Furthermore, by varying the thickness of the hypodermis (poorly conductive fatty tissue) it has been shown that this skin layer is responsible for the edge effect itself as well as the pronouncement thereof.

The impedance of the neutral electrode has another important impact on the current distribution with respect to the edge effect. The higher the ohmic resistance of the neutral electrode, the less pronounced is the edge effect and the higher is the self-heating because of a power drop at the neutral electrode itself. Modern, single-use, self-adhesive neutral electrodes have an impedance of less than 200 ohms/$cm^2$, a noticeable self-heating, however, only occurs at 2000 ohms/$cm^2$ or more.

The electronic simulation of the simplified plane model allows further simplifications of the resistance network. These are achieved by combining the resistances in series and eliminating negligible resistances. For instance, the horizontal equivalent resistance 31 (Rh) of the epidermis (100 kohms) against the horizontal equivalent resistance 31 (Rh) of the corium adjacent thereto (1 ohm) may be neglected and therefore eliminated. With each further simplification step it has to be checked whether the required properties still correspond to the complete cylinder model and to the measuring results with subjects after this step.

Figure 4:
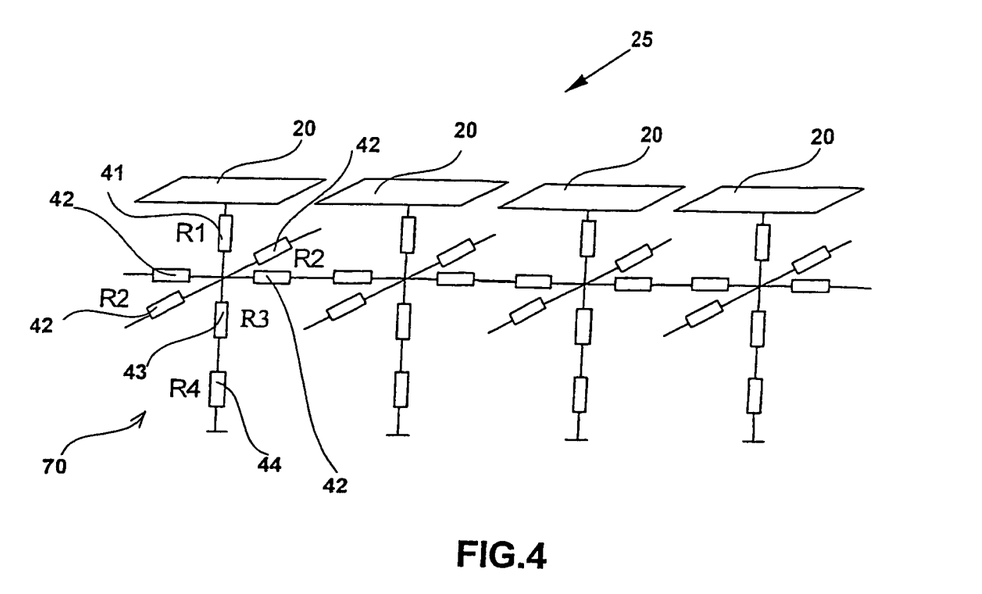
FIG. 4 shows a part of a circuit arrangement in which measuring prism cells are formed by resistances.

In order to circumvent experimental set-ups for each intermediate step, the resistance combination was simulated by means of the program Matlab, and the currents, voltages and dissipation powers for each branch were calculated. The result of this simplification is a measuring surface 25 in which each measuring prism cell is formed by a combination of seven resistances, as is shown in FIG. 4.

Here, the horizontal equivalent resistance 31 (Rh) of the epidermis of the model shown in FIG. 3 is eliminated. The equivalent resistance 41 (R1) is a combination of the vertical equivalent resistance 2× Rz of the epidermis and the vertical equivalent resistance Rz of the corium, and the equivalent resistances 42 (R2) correspond to the horizontal equivalent resistances 31 (Rh) of the corium. The equivalent resistance 43 (R3) is the remaining vertical equivalent resistance Rz of the corium, and the equivalent resistance 44 (R4) is the vertical equivalent resistance of the hypodermis. The horizontal equivalent resistance Rh of the hypodermis was neglected. The common ground connected to the equivalent resistance 44 (R4) corresponds to the highly conductive muscle volume.

Figure 5:
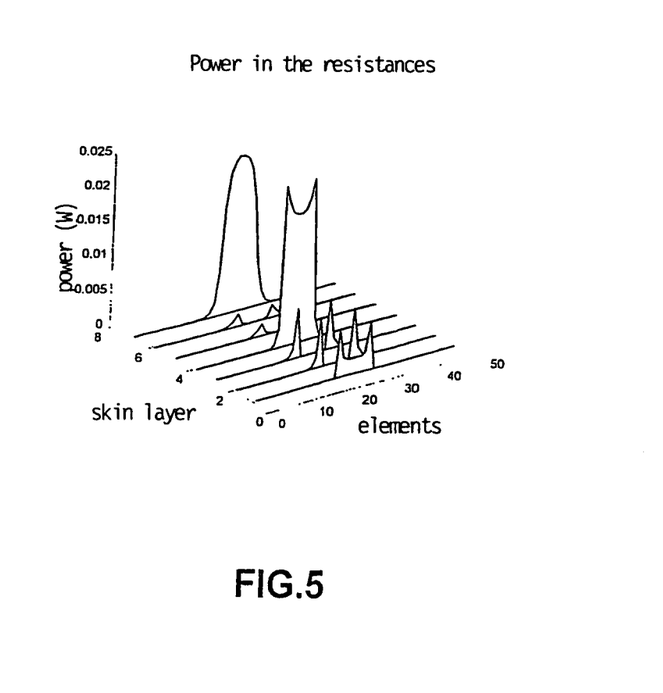
FIG. 5 shows a distribution of dissipation power in simulate skin layers of a simplified equivalent resistance model.

The distribution of dissipation power in the simulated skin layers of the simplified equivalent resistance model calculated by means of Matlab is shown in FIG. 5. This model calculation shows that the corium constitutes the main heat source. The value designated as "element" in FIG. 5 corresponds to the measuring prism cells formed by the equivalent resistances. The dissipation power in the hypodermis is distributed within a much larger volume, so that the resulting temperature increase is significantly lower than in the corium.

Figure 6:
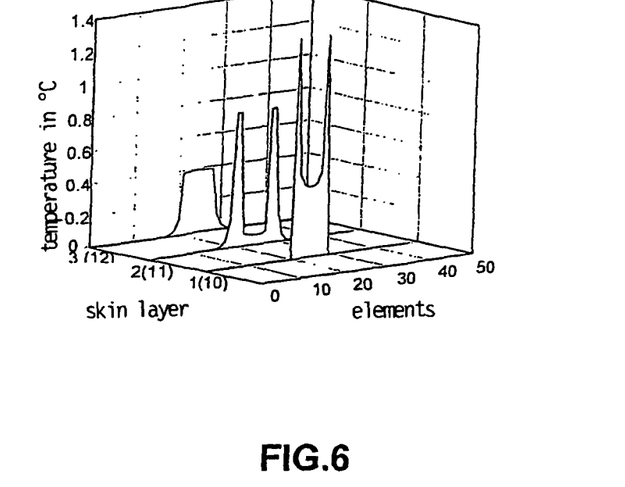
FIG. 6 shows a graph of temperature distribution against the skin layer and the elements.

The calculated dissipation power distribution allows an estimation of the temperature in the skin layers, based on the assumption that basically water in the skin is heated. The conversion factor between energy loss (product of power and time) and temperature increase (0° C.) is 4.193° C./Ws, and a corresponding graph of the temperature distribution against the skin layer and the elements is shown in FIG. 6. Skin layer 1 (10) is the epidermis, skin layer 2 (11) is the corium, and skin layer 3 (12) is the hypodermis.

The temperature increase shows the desired edge effect, which is significantly broader in the corium 11 than in the epidermis 10 (FIG. 2). The temperature increase in the hypodermis 12 plays only a minor role because it is distributed within a much larger volume. By comparison, the corium 11 has an average thickness of 1.5 mm, while the hypodermis has an average thickness of 10 to 30 mm.

The actually realized equivalent resistance circuit, however, does not heat a water volume, but the respective equivalent resistance representing this volume. For the corium volume to be assumed for each measuring electrode (1 cm$^2$×1.5 mm), the temperature increase measured at the equivalent resistance has to be multiplied by a conversion factor of 1.73 in order to obtain the temperature increase of the water volume at the same energy.

BRIEF DESCRIPTION OF THE DRAWINGS

In the following, the invention is explained in greater detail with reference to the exemplary embodiments shown in the drawings.

DETAILED DESCRIPTION OF THE INVENTION

In the present invention, the calculated model (cylinder model and plane model) as well as experiments with subjects have shown that energy loss in the hypodermis, which is approximately constant across the entire surface of the neutral electrode (FIG. 6), is irrelevant for the resulting temperature increase because of the large volume of this skin layer. This effect is clearly pronounced in the hypodermis, may, however, also occur in other skin layers.

One possibility to simulate this effect comprises the provision of an equivalent resistance especially for the hypodermis, wherein this equivalent resistance is, however, situated outside the spatial measuring range of the temperature sensor associated with the respective measuring electrode, so that it cannot contribute to the temperature increase. In practice, this leads to a plurality of conducting lines in the periphery of the measuring surface, and a realization is only possible with laborious manufacturing techniques and cost-intensive multilayer circuit boards.

Consequently, the present invention aims at the provision of a device according to the above description which allows the simulation of the dissipation power occurring in a skin layer without contributing to the overall temperature increase of individual measuring prism cells.

According to the invention this is achieved in that at least one resistance of the equivalent resistance circuit is formed by a reactive resistance.

By providing at least one resistance of the equivalent resistance circuit in the form of a reactive resistance, the application of an alternating voltage to the equivalent resistance circuit does not lead to any dissipation power at the reactive resistance. Consequently, its temperature does not increase. The reactive resistance may therefore be arranged within the immediate vicinity of the measuring electrode and the corresponding temperature sensor. Furthermore, the value of the reactive resistance may be varied by changing the frequency of the voltage applied to the equivalent resistance circuit. Thus, the impedance of the respective skin layer, for which a reactive resistance is intended, and its thickness may be easily changed in a simulation by varying the frequency.

The reactive resistance can basically be an inductance, a capacitance or a combination of these. According to a further embodiment of the invention, a high miniaturization degree can easily be achieved by providing a capacitor as reactive resistance.

Since the hypodermis has a relatively large thickness compared to the other skin layers and therefore only plays a minor role in the overall temperature increase of all layers below the neutral electrode, according to a preferred embodiment of the invention, the resistance of the equivalent resistance circuit representing the hypodermis may be formed by the reactive resistance.

A simulation of different skin thicknesses may be achieved by varying the frequency of the alternating voltage source connected to the neutral electrode when it is applied, which is why, according to another embodiment, the alternating voltage source has a variable frequency.

Furthermore it has proven advantageous to arrange the measuring electrodes with the associated equivalent resistance circuits in the form of a matrix of columns and rows. The advantages of such a matrix arrangement are a simplification of temperature measurements by means of a matrix scan of the temperature sensors and a measuring surface layout which can be produced relatively easily.

By applying the principle of the invention to the equivalent resistance model with six resistances, according to another embodiment of the invention, each equivalent resistance circuit has a central node which is connected to one terminal each of four horizontal equivalent resistances and to one terminal each of a first and a second vertical equivalent resistance, wherein the other ends of the horizontal equivalent resistances are connected to the horizontal equivalent resistances of the equivalent resistance circuits adjacent in the column and row directions, and wherein the other terminal of the first vertical equivalent resistance is connected to the measuring electrode and the other terminal of the second vertical equivalent resistance is connected to ground via the reactive resistance. Consequently, in this embodiment of the invention, the vertical equivalent resistance of the hypodermis of the model reduced to seven resistances (FIG. 4) is replaced by the reactive resistance, which thus does not contribute anymore to the overall temperature increase of the individual measuring prism cells.

Since in experimental measurements with patients a temperature increase beyond the edges of the neutral electrode was detected, this was simulated by means of additional equivalent resistances, which are, however, not connected directly to the measuring electrodes of the measuring surface. In order to achieve this, according to another embodiment of the invention, the equivalent resistance circuits associated with the measuring electrodes arranged along the periphery of the measuring surface are each connected to a peripheral impedance circuit with at least one associated temperature sensor, wherein the peripheral impedance circuit is connected to the terminal of the horizontal equivalent resistance, which is unconnected at the periphery, of the equivalent resistance circuit associated with the measuring electrode situated at the periphery of the measuring surface.

Consequently, further equivalent resistance elements with temperature sensors have to be arranged outside the actual measuring surface in order to enable an infinite representation of the volume conductor. In this connection, in another embodiment of the invention, each peripheral impedance circuit may consist of one or more, preferably two, serially connected peripheral cells, wherein each peripheral cell has a central node connected to one terminal each of four horizontal peripheral resistances, which correspond to the horizontal equivalent resistances, and to the terminal of a vertical peripheral resistance, which corresponds to the second vertical equivalent resistance, wherein the other ends of the horizontal peripheral resistances are connected to the horizontal equivalent resistance or the horizontal peripheral resistance of the equivalent resistance circuits or peripheral cells adjacent in the column and row directions, and wherein the other terminal of the vertical peripheral resistance is connected to ground via the reactive resistance.

The patient's skin, however, extends beyond the immediate periphery of the neutral electrode, in which a heating effect can be measured, and this skin volume outside the immediate neutral electrode area leads to a current flow, albeit a minor one, just like the one directly below the neutral electrode, which in fact does not play a role for the temperature increase of the skin, does, however, influence the overall current distribution. This additional current component could be simulated by another serial connection of peripheral cells. However, in order to keep the measuring circuit board small in size, it may be provided that the peripheral impedance circuit is connected to ground via a terminal resistance circuit. Preferably, the terminal resistance circuit is dimensioned to allow the current of 15 to 20 peripheral cells to flow through it, which guarantees that the simulation takes into consideration a relatively large surface around the neutral electrode area.

As mentioned above, when neglecting the horizontal equivalent resistances of the muscle tissue layer in the equivalent resistance circuit, the directional dependence of the temperature distribution is lost. An electronic realization would result in four further equivalent resistances per measuring prism cell. Due to symmetric considerations, however, they could be reduced to a single resistance for each measuring prism cell, wherein according to another embodiment of the invention, for each row or each column of the matrix of measuring electrodes and associated equivalent resistance circuits a common horizontal equivalent resistance representing the muscle layer is provided, which is arranged outside the spatial measuring range of the temperature sensor.

An advantageous circuit engineering variation of the device according to the invention may consist in that one terminal of the common horizontal equivalent resistances is connected to the equivalent resistance circuits associated with the measuring electrodes of the row or of the column. This leads to a substantial simplification of the layout of the connecting lines.

Modern generators for use in electrosurgery comprise a measuring circuit which allows the measurement of the contact quality between the patient's skin and the neutral electrode during a surgery by using a split neutral electrode (COM). For instance, a voltage is applied to both halves of the neutral electrode, and the resulting impedance is determined. An increase of the impedance value above a predeterminable threshold value, e.g. due to the detachment of part of the neutral electrode from the patient's skin, causes an alarm in the electrosurgical device. The risk of burns because of a partial detachment of the neutral electrode from the patient's skin is thus avoided. To date, functional tests for such monitoring circuits have had to be conducted on test persons as well. Consequently, one object of the invention concerns the possibility of conducting such functional tests not on human beings, but by means of a device with exactly predeterminable test conditions.

According to the present invention this is achieved by using a device according to the invention for checking the neutral electrode contact quality monitoring circuit (CQM) of an electrosurgical apparatus.

With the skin simulation by means of the device according to the invention, a CQM circuit may be tested under controlled conditions, wherein the equivalent resistance circuits of the measuring electrodes and, as appropriate, the terminal resistance circuits together give the test impedance. Here, the device according to the invention is operated passively, i.e. without the application of a voltage between the neutral electrode and the resistance network of the equivalent resistance circuits.

Furthermore, the invention concerns a device for testing a neutral electrode for use in electrosurgery, comprising a measuring surface which is formed by a plurality of measuring electrodes, whereon the neutral electrode may be applied, wherein each measuring electrode of the measuring surface is connected to an equivalent resistance circuit representing at least one layer of the human skin, e.g. the epidermis, the corium and the hypodermis including fatty tissue, and consisting of at least two resistances, which equivalent resistance circuit is in thermal contact with at least one temperature sensor, wherein the measuring electrodes are provided on one side of a measuring circuit board forming the measuring surface and the resistances of the associated equivalent resistance circuits are arranged on the opposite side of the measuring circuit board.

Devices of this kind in use so far have the disadvantage that the equivalent resistances provided on the measuring circuit board between the temperature sensors also provided on the measuring circuit board radiate their dissipation power towards the temperature sensors of the adjacent measuring prism cells as well, which leads to measuring errors.

One object of the invention therefore consists in the provision of a device mentioned above, by means of which the temperature increase of individual measuring cells caused by equivalent resistance circuits may be measured as precisely as possible without influencing the respective adjacent equivalent resistance circuit.

According to the invention, this is achieved by arranging the temperature sensors on a further circuit board which is spaced from the measuring circuit board by a drilled board provided with through holes, wherein the temperatures sensors facing the resistances of the equivalent resistance circuits project into the through holes of the drilled board.

Thus, the temperature sensors are arranged opposite to the respective equivalent resistance circuits and spaced by means of the drilled board. The impact of adjacent measuring prism cells on the determination of the cell temperature may thus be strongly reduced.

If the measuring electrodes are arranged in the form of a matrix, according to another aspect of the invention the through holes of the drilled board may be arranged concentrically with the centers of the measuring electrodes.

According to another embodiment of the invention, the desired heat conduction between the temperature sensors and the respective equivalent resistance circuits may be increased significantly if the space between the resistances of the equivalent resistance circuits and the temperature sensors within the through holes is filled with a heat-conducting material.

A protection of adjacent measuring prism cells against heat transport, which is also desirable, may by achieved if the space between the resistances of the equivalent resistance circuits is filled with a heat-insulating material.

Furthermore, an extensive miniaturization of the components required for the construction of the device according to the invention may be achieved if the resistances of the equivalent resistance circuits and the temperature sensors are formed by SMD components.

An extremely dense packing of equivalent resistances is also part of the measures which result in an improvement of the temperature-related separation of individual measuring prism cells. One variation of the invention may thus consist in that the resistances of the equivalent resistance circuits are arranged in the immediate vicinity of the associated measuring electrode on the opposite side of the measuring circuit board and are connected to it via at least one feedthrough.

Figure 1:
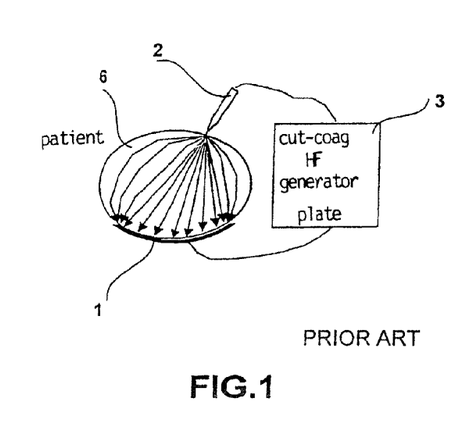
FIG. 1 shows a sectional drawing of a monopolar technique.
Figure 7:
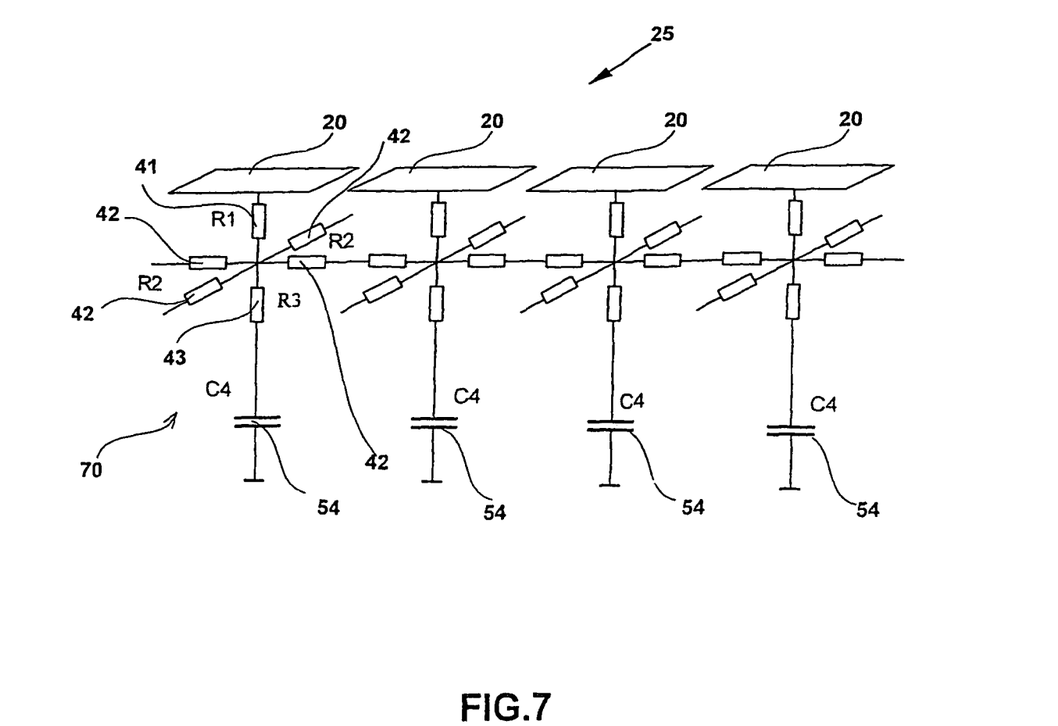
FIG. 7 shows a part of a circuit arrangement for an embodiment of the device according to the invention.

FIG. 7 shows a device for testing a neutral electrode for use in electrosurgery not shown, as is for instance described with regard to the arrangement shown in FIG. 1, comprising a measuring surface 25 which is formed by a plurality of measuring electrodes 20, whereon the neutral electrode may be applied. Here, the measuring electrodes 20 with the associated equivalent resistance circuits 70 are preferably arranged in the form of a matrix of columns and rows, wherein FIG. 7 shows only a part of a row.

According to the invention, at least one resistance of each equivalent resistance circuit 70 is formed by a reactive resistance 54.

Preferably, each equivalent resistance circuit 70 according to FIG. 7 has a central node which is connected to one terminal each of four horizontal equivalent resistances 42 and with one terminal each of a first and a second vertical equivalent resistance 41, 43. The other ends of the horizontal equivalent resistances 42 are connected to the horizontal equivalent resistances 42 of the equivalent resistance circuits 70 adjacent in the column and row directions, while the other terminal of the first vertical equivalent resistance 41 is connected to the measuring electrode 20 and the other terminal of the second vertical equivalent resistance 43 is connected to ground via the reactive resistance 54. Of course, the interconnection and dimensional design of the resistances of the equivalent resistance circuit 70 can vary, because the implementation of the principle of the invention is based on the reactive resistance 54.

A possible variation of the formation of the measuring surface 25 comprises the provision of the measuring electrodes 20 in the form of preferably square areas 1 $Cm^2$ in size which are electrically insulated from each other on a measuring circuit board not shown in FIG. 7 and the provision of the measuring electrodes 20 with feedthroughs via which each measuring electrode 20 of the measuring surface 25 is connected to the equivalent resistance circuit 70 representing at least one layer of the human skin, e.g. the epidermis, the corium and the hypodermis including fatty tissue, which is in thermal contact with at least one temperature sensor not shown in FIG. 7. The equivalent resistances 41, 42, 43, 54 of the equivalent resistance circuit 70 are preferably SMD components soldered onto the measuring circuit board on the side facing away from the measuring electrodes 20 and connected to the measuring electrodes 20 via the respective feedthroughs. Any other design of the measuring surface 25 with the equivalent resistance circuits 41, 42, 43, 54 of equal utility for persons skilled in the art may also constitute a basis for further embodiments of the invention.

Preferably, the temperature sensors in thermal contact with the equivalent resistance circuits are formed in a generally known manner by bipolar transistors.

In the exemplary embodiment of FIG. 7, the equivalent resistance 44 of the equivalent resistance circuit 70 provided in FIG. 4 is replaced by a capacitor 54 whose reactive resistance value depends on the frequency and is $Rc=1/(j.\omega.C)$, i.e. is inversely proportional to the capacitance and to the frequency of an applied alternating signal ($\omega=2\pi.f$). According to FIG. 7, the capacitor 54 as reactive resistance thus replaces the ohmic resistance 44 which, according to FIG. 4, represents the hypodermis layer 12 (FIG. 2) of the individual measuring prism cells and does not produce any dissipated heat within the equivalent resistance circuit 70, which is why the capacitor 54 may be situated in the vicinity of the temperature sensor not shown without contributing to a temperature increase thereof. Consequently, like the other equivalent resistances 41, 42, 43 of the individual measuring prism cells, the capacitor 54 may be arranged on the measuring circuit board in the form of SMD components.

By varying the frequency of the applied current, the reactive resistance value of the capacitor 54 can by changed in order to simulate different thicknesses of the hypodermis 12 (FIG. 2). Consequently, it is advantageous to apply an alternating voltage between the neutral electrode and the equivalent resistance circuits 70 via an alternating voltage source with variable frequency, in order to be able to simulate different thicknesses of the hypodermis 12 by varying the applied alternating voltage.

The capacitance of the capacitor 54 is to be determined under the consideration of the frequency of the alternating current source by means of which the device according to the invention is operated. Instead of the capacitor 54, the invention also allows the use of an inductance as reactive resistance in the equivalent resistance circuit 70.

Furthermore, the provision of a reactive resistance in the equivalent resistance circuit allows the simulation of other layers than the hypodermis layer 12 (FIG. 2). In addition, the invention, especially the replacement of an ohmic resistance by a reactive resistance, may also be used for other circuit arrangements than shown in FIG. 4 and FIG. 7.

Cross-linking individual partial prism cells via the horizontal equivalent resistances 42 for simulating the corium 11 (FIG. 2), as is shown in FIG. 7, results in corresponding cross currents and, in accordance with the model calculation, in a pronounced edge effect, which may be varied by changing the frequency of the voltage applied to the equivalent resistance circuit 70 via the neutral electrode and the measuring electrode 20, since the impedance of the reactive resistance 54 representing the hypodermis 12 changes according to the frequency, so that different hypodermis thicknesses result in different edge effects.

With a patient, the temperature increase in the peripheral area of the neutral electrode caused by the edge effect extends beyond the area of the neutral electrode 1 itself, which is why the AAMI HF-18 standard specifies a temperature measurement on an area extending beyond the neutral electrode surface. For electronic simulations this means that additional equivalent resistances have to be provided in the periphery of the neutral electrode 1, outside the actual measuring surface, in order to represent a quasi infinite volume conductor.

Figure 13:
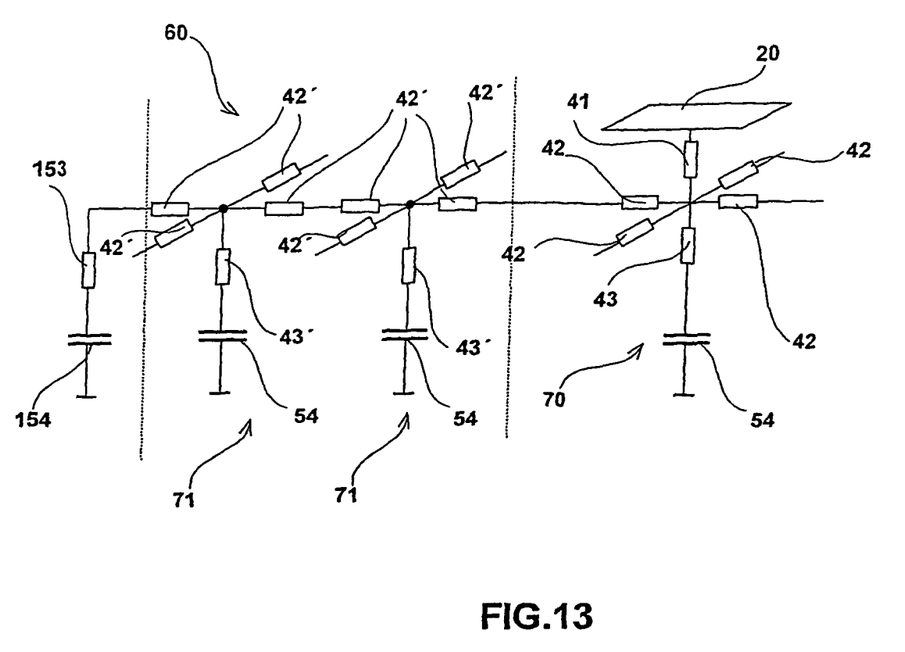
FIG. 13 shows a part of a circuit arrangement of another embodiment of the device according to the invention.

For this purpose, the equivalent resistance circuits 70 associated with the measuring electrodes 20 arranged along the periphery of the measuring surface 25 are each connected to a peripheral impedance circuit 60, as is shown in FIG. 13. For measuring the temperature increase caused by the peripheral impedance circuit 60, a temperature sensor associated therewith is provided.

Here, the terminal impedance circuit 60 is connected to the terminal of the horizontal equivalent resistance 42, which is unconnected at the periphery, of the equivalent resistance circuit 70 associated with the measuring electrode 20 situated at the periphery of the measuring surface 25, and it consists of one or more—preferably, as is shown in FIG. 13, two—serially connected peripheral cells 71 which are not directly connected to measuring electrodes 20. The measurement of the temperature of the terminal cells 71 is achieved by means of further temperature sensors not shown in FIG. 13.

The two peripheral cells 71 have a central node which is connected to one terminal each of four horizontal peripheral resistances 42', which correspond to the horizontal equivalent resistances 42, and to one terminal of a vertical peripheral resistance 43', which corresponds to the second vertical equivalent resistance 43. The other ends of the horizontal peripheral resistances 42' are connected to the horizontal equivalent resistance 42 or the horizontal peripheral resistance 42' of the equivalent resistance circuits 70 or peripheral cells 71 adjacent in the column and row directions. Finally, the other terminal of the vertical peripheral resistance 43' is connected to ground via the reactive resistance 54.

The reason why two peripheral cells 71 are connected in series concerns the heating effect measurable in practice which is determinable up to a distance of about 2 cm. Since each peripheral cell 71 extends over 1 cm in a direction perpendicular to the edge of the neutral electrode, a cell number of 2 is obtained. With other divisions of the measuring surface, the number of terminal cells 71 to be combined varies.

Next to the periphery around the neutral electrode, in the skin volume around it, there is also a current flow which does not contribute to the heating, does, however, being part of the total current, reduce the current flowing through the neutral electrode area. It has been shown that the current flowing through the, compared to the neutral electrode surface, infinitely expanded skin may be appropriately simulated by 15 to 20 peripheral cells. Each peripheral impedance circuit 60 is thus connected to ground via a terminal impedance circuit 153, 154, wherein the dimensions are chosen to allow a current corresponding to 15 to 20 peripheral cells to flow through it. The invention allows for a variation of the number of peripheral cells simulated by the terminal impedance circuit, which in FIG. 13 consists of a series connection of a terminal resistance 153 and a capacitor 154, according to the circumstances.

In the equivalent resistance circuits of FIG. 4, muscle tissue is simulated by an equipotential surface which is realized by the connection of the vertical equivalent resistances 44 to ground. In the highly conductive muscle tissue, the horizontal equivalent resistances Rh (FIG. 3) are assumed to have 0 ohm, which is why the directional dependency described above is not passed on in the model and is, because of stronger heating, more strongly pronounced at the edge of the neutral electrode closer to the surgical site.

Figure 8A:
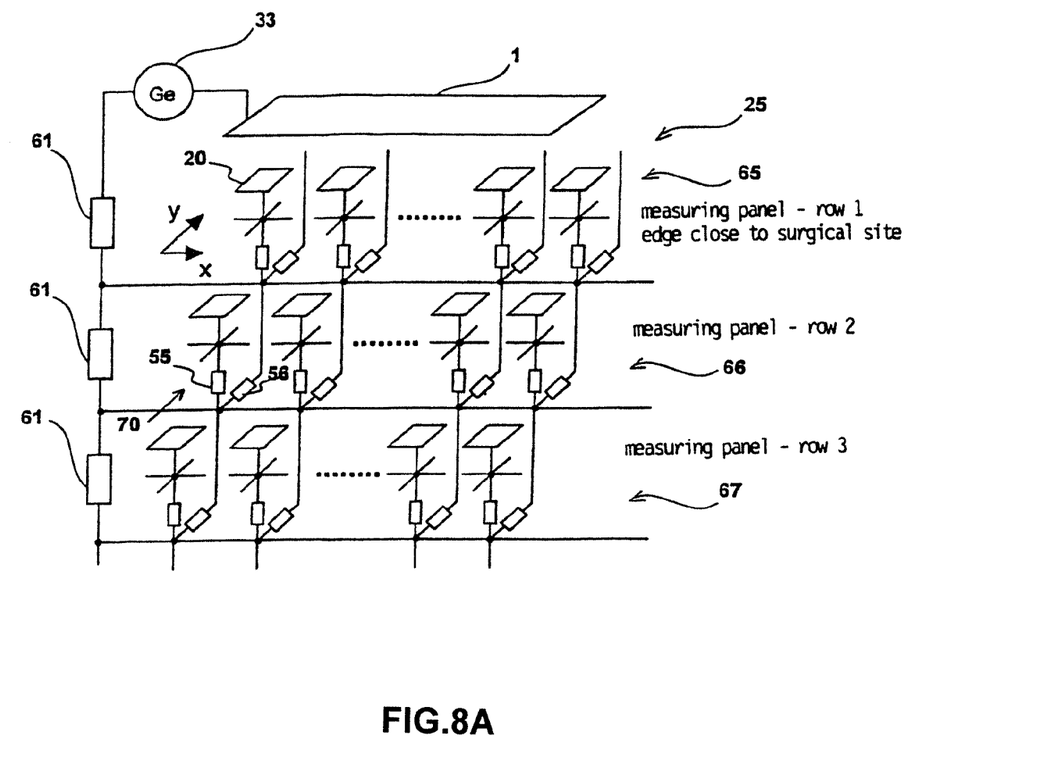
FIGS. 8A and 8B shows a part of a circuit arrangement for another embodiment of the device according to the invention.
Figure 8B:
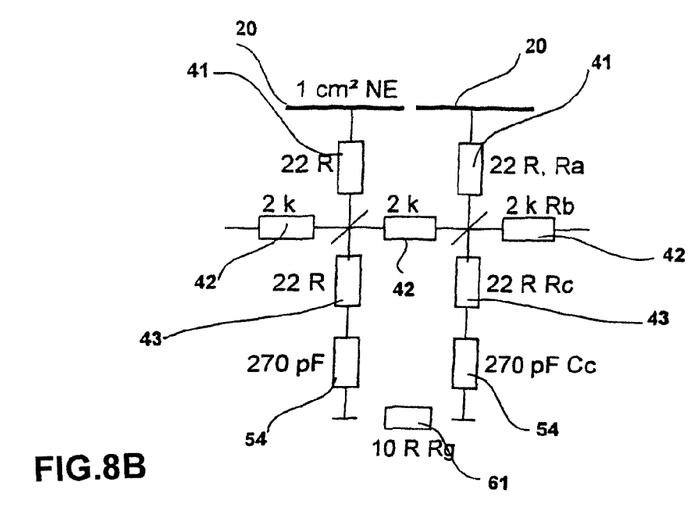

A complete electronic simulation of directional dependence would require four further equivalent resistances Rh far each measuring electrode. Because of symmetric reasons, however, cross currents flow to the surgical site in the muscle in only one horizontal direction, e.g. in the direction of the columns (y direction), which is why the horizontal equivalent resistances in the direction of the row (x direction) may be neglected and all equivalent resistances 56 positioned in one row of the measuring electrode matrix may be combined in one equivalent resistance 61, which may be positioned outside the measuring range of the temperature sensor, as is shown in the exemplary embodiment of FIGS. 8A and 8B, where the vertical resistances 43, 54 are represented as impedance 55 and the horizontal resistances Rh of the muscle tissue in the column direction are represented as resistances 56. A voltage source 33 for operating the device according to the invention is arranged between the neutral electrode 1 and the horizontal equivalent resistances 61, which represent the horizontal resistances Rh of the muscle tissue in the column direction, are positioned outside the spatial measuring range of the temperature sensor, and do thus not influence the temperature measurement. The invention also allows the exchange of the x and y directions, which requires the outside arrangement of the horizontal resistances Rh for the row direction of the measuring electrode matrix.

In connection with the use of a split neutral electrode for electrosurgical purposes, usually a so-called CQM (contact quality monitoring) test is performed in order to determine the quality of the contact between the patient's skin and the neutral electrode during a surgery. For instance, a voltage may be applied to both halves of a neutral electrode split in two and the resistance may be determined from the current flow. This measurement technique may, however, also be used for neutral electrodes split into multiple parts. To date, CQM functional tests have had to be conducted on subjects.

One embodiment of the invention consists in the use of the device according to the invention for testing the neutral electrode contact quality monitoring circuit (CQM) of an electrosurgical apparatus. Here, the device according to the invention is operated passively without a voltage source and simulates the impedance of a skin section. For this purpose, a neutral electrode to be tested is applied to the device according to the invention and the CQM test is performed. This allows the testing of this monitoring circuit under controlled conditions, wherein the impedance network consisting of the individual equivalent resistance circuits and, if appropriate, of the peripheral and terminal impedance circuits is used as test impedance.

Figure 12:
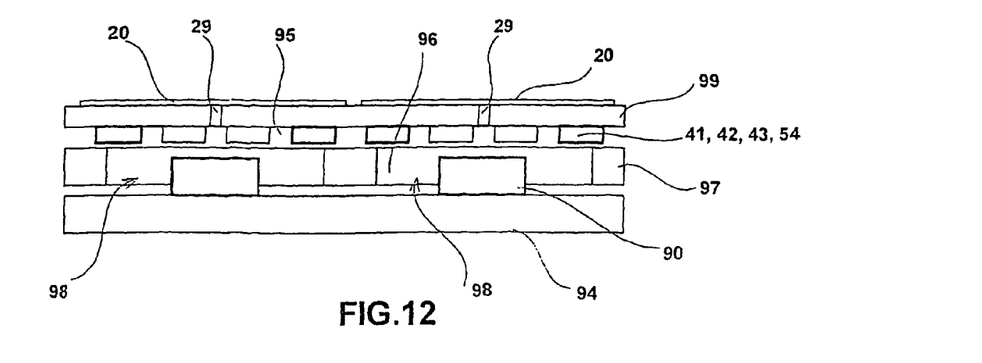
FIG. 12 shows a sectional view of a part of the embodiment of the device according to the invention shown in FIGS. 10 and 11.

The arrangement of the resistances of the equivalent resistance circuit 70 is of major importance for a proper functioning of the device according to the invention. A preferred arrangement of equivalent resistances and temperature sensors is shown in FIG. 12. The measuring electrodes 20 are provided on one side of a measuring circuit board 99 forming the measuring surface 25, and the resistances 41, 42, 43, 54 of the equivalent resistance circuits 70 associated with the measuring electrodes 20 are provided on the opposite side of the measuring circuit board 99.

Figure 10:
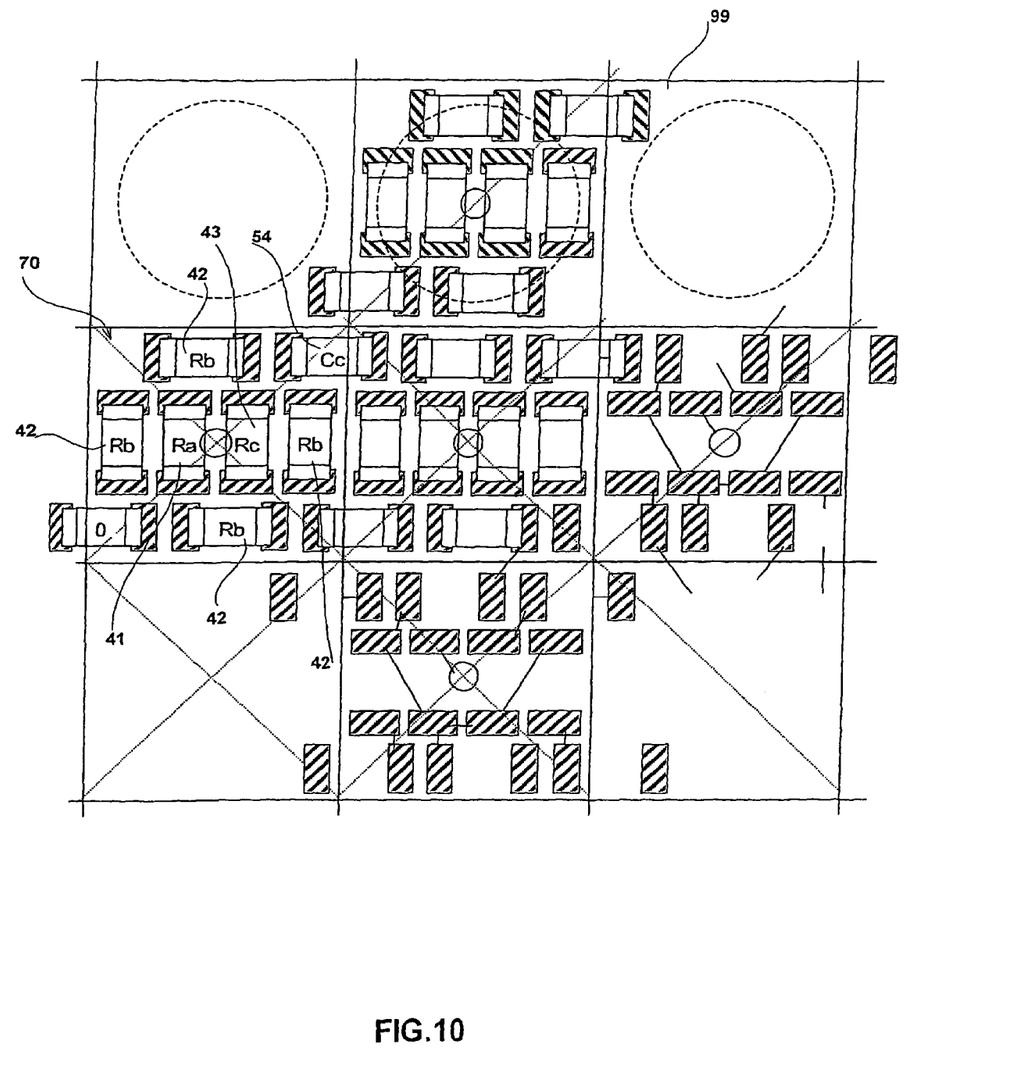
FIG. 10 shows a detailed view of a layout for a measuring circuit board of another embodiment of the device according to the invention.
Figure 11:
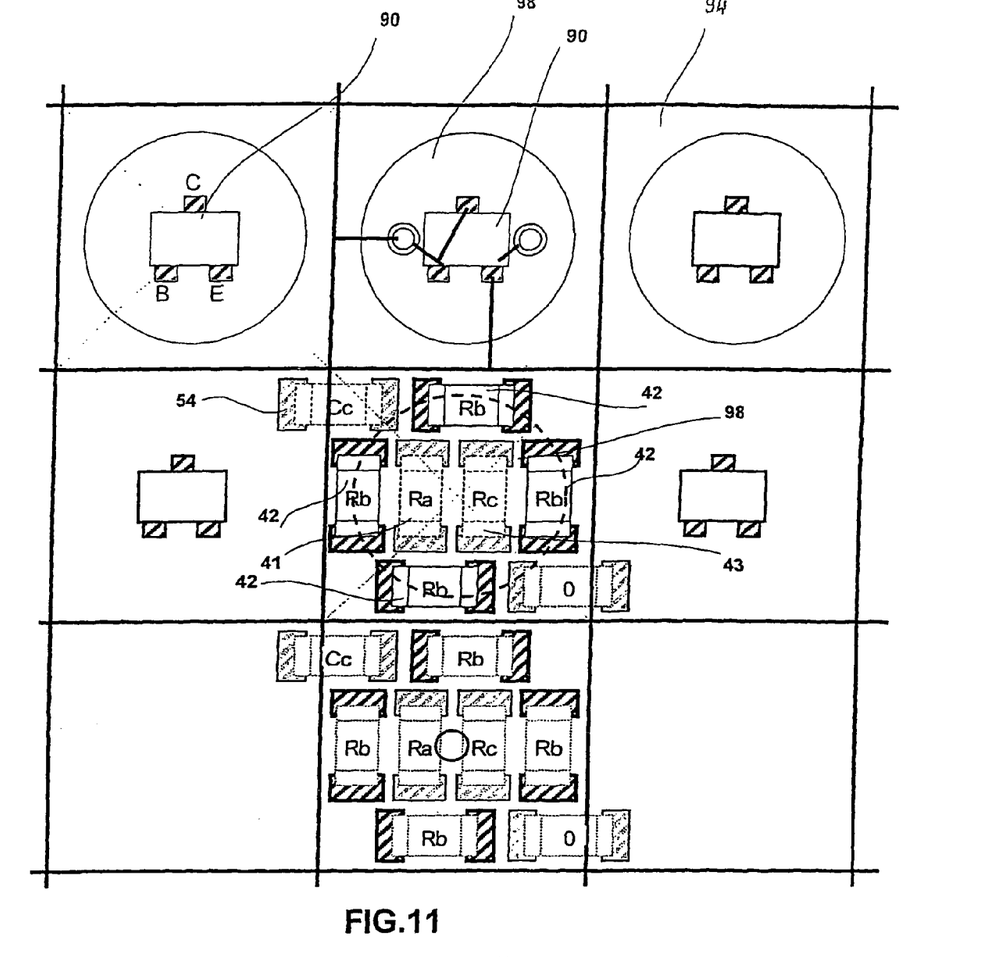
FIG. 11 shows a detailed view of a layout for the measuring circuit board of FIG. 10 as well as another circuit board with temperature sensors.

According to the invention, the temperature sensors 90 are provided on a further board 94 which is spaced from the measuring circuit board 99 by a drilled board 97 provided with through holes 98. The temperature sensors 90 facing the resistances 41, 42, 43, 54 of the equivalent resistance circuit 70 project into the through holes 98 of the drilled board 97. The layout representations of FIGS. 10 and 11 show that the measuring electrodes 20 not shown are arranged in the form of a matrix, and the through holes 98 of the drilled board 97 are arranged concentrically with the measuring electrode centers. The space between the resistances 41, 42, 43, 54 of the equivalent resistance circuits 70 and the temperature sensors 90 within the through holes 98 is filled with a heat-conducting material, preferably a heat-conducting paste, which holds together the measuring circuit board 99, the additional circuit board 94 and the drilled board 97 by means of its adhesive properties and passes on almost all of the dissipation power to the temperature sensors 90 because of its good heat conductivity, thus contributing to the avoidance of measurement errors.

Since the equivalent resistances 41, 42, 43 dissipate heat also sidewards to the directly adjacent equivalent resistances, the space between the resistances 41, 42, 43, 54 of the equivalent resistance circuits 70 is preferably filled with a heat-insulating material.

Figure 9:
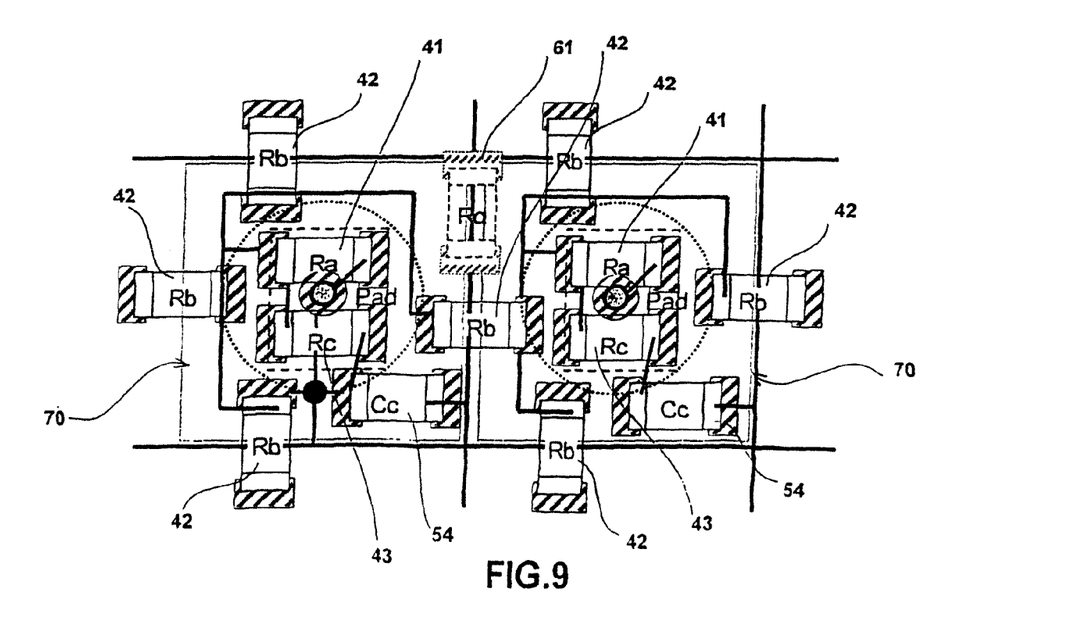
FIG. 9 shows a part of a circuit arrangement for another embodiment of the device according to the invention and detailed view of a corresponding layout for a measuring circuit board.

Preferably, the equivalent resistances 41, 42, 43, 54 of the equivalent resistance circuits 70 and the temperature sensors are formed by SMD components, as may be seen in FIGS. 9 to 11. The embodiment shown in FIG. 9 has the disadvantage that the equivalent resistances 42 are arranged relatively far from the temperature sensors and thus also contribute to a temperature increase of the respective adjacent measuring electrodes 20. This situation may be improved by arranging the equivalent resistances of the equivalent resistance circuits 70 in the immediate vicinity of the corresponding measuring electrode 20 on the opposite side of the measuring circuit board 99, as is shown in FIGS. 10 and 11. A measuring electrode 20 is connected to the corresponding equivalent resistance circuit 70 via at least one feedthrough 29. A dense packing of the equivalent resistances in the area of the measuring electrode 20 makes sure that adjacent equivalent resistance circuits 70 have only minor impact.

The invention claimed is:

1. A device for testing a neutral electrode for use in electrosurgery, comprising a measuring surface which is formed by a plurality of measuring electrodes whereon the neutral electrode may be applied, wherein each measuring electrode of the measuring surface is connected to a respective equivalent resistance circuit configured to represent layers of the human skin comprising at least the hypodermis including fatty tissue, wherein each respective equivalent resistance circuit has at least two resistances with at least one resistance of the at least the at least two resistances being formed by a reactive resistance configured to represent the hypodermis including fatty tissue and further configured to vary the thickness of the hypodermis including fatty tissue without an increase in temperature of the reactive resistance, and wherein each equivalent resistance circuit is in thermal contact with at least one temperature sensor having a spatial measuring range.

2. The device according to claim 1, characterized in that the reactive resistance is formed by a capacitance.

3. The device according to any one of claims 1 to 2, wherein the device is connectable to an alternating voltage source having a variable frequency when the neutral electrode is applied to the measuring surface.

4. The device according to any one of claims 1 to 2, characterized in that the plurality of measuring electrodes with their respective equivalent resistance circuits are arranged in the form of a matrix of columns and rows.

5. The device according to claim 4, characterized in that the at least two resistances of each equivalent resistance circuit include four horizontal equivalent resistances each having a first terminal and a second terminal, a first vertical equivalent resistance having a first terminal and a second terminal, and a second equivalent resistance having a first terminal and a second terminal; wherein each equivalent resistance circuit has a central node which is connected to the first terminal of each of the four horizontal equivalent resistances, the first terminal of the first vertical equivalent resistance, and the first terminal of the second vertical equivalent resistance; wherein each of the second terminals of the horizontal equivalent resistances are connected to a respective one of the horizontal equivalent resistances of the equivalent resistance circuits in adjacent columns and rows in the matrix; wherein the second terminal of the first vertical equivalent resistance is connected to a respective one of the plurality of measuring electrodes; and wherein the second terminal of the second vertical equivalent resistance is connected to ground via the reactive resistance.

6. The device according to claim 4, characterized in that the equivalent resistance circuits of the measuring electrodes arranged along the periphery of the measuring surface are each connected to a peripheral impedance circuit having at least one temperature sensor.

7. The device according to claim 6, characterized in that each respective peripheral impedance circuit is connected to the second terminal of a horizontal equivalent resistance which is unconnected at the periphery.

8. The device according to claim 6, characterized in that each peripheral impedance circuit consists of two, serially connected peripheral cells, wherein each peripheral cell has a central node connected to a terminal of each of four horizontal peripheral resistances and to a terminal of a vertical peripheral resistance, wherein the four horizontal peripheral resistances correspond to the four horizontal equivalent resistances of the respective equivalent resistance circuit connected to the peripheral impedance circuit, wherein the vertical peripheral resistance corresponds to the second vertical equivalent resistance of the respective equivalent resistance circuit connected to the peripheral impedance circuit, wherein second terminals of each of the four horizontal peripheral resistances are connected to one of a horizontal equivalent resistance of the equivalent resistance circuits and a horizontal peripheral resistance of the peripheral cells located in the adjacent column and row directions, and wherein a second terminal of the vertical peripheral resistance is connected to ground via the reactive resistance.

9. The device according to claim 6, characterized in that each peripheral impedance circuit is connected to ground via a terminal resistance circuit.

10. The device according to claim 4, characterized in that for each row or each column of the matrix of the plurality of measuring electrodes and respective equivalent resistance circuits, a common horizontal equivalent resistance configured to represent the layers of the human skin is provided which is arranged outside of the spatial measuring range of the at least one temperature sensor.

11. The device according to claim 10, characterized in that a first terminal of the common horizontal equivalent resistance is connected to the equivalent resistance circuits associated with the measuring electrodes of the respective row or of the respective column.

12. The device according to any one of claims 1 to 2, characterized in that the at least one temperature sensor is formed by a bipolar transistor.

13. A method of use of device for testing a neutral electrode for use in electrosurgery, the device comprising a measuring surface which is formed by a plurality of measuring electrodes whereon the neutral electrode may be applied, wherein each measuring electrode of the measuring surface is connected to a respective equivalent resistance circuit configured to represent layers of the human skin comprising at least the hypodermis including fatty tissue, wherein each respective equivalent resistance circuit has at least two resistances with at least one resistance of the at least two resistances being formed by a reactive resistance configured to represent the hypodermis including fatty tissue and wherein each equivalent resistance circuit is in thermal contact with at least one temperature sensor; the method comprising monitoring a neutral electrode contact quality monitoring circuit (CQM) of an electrosurgical apparatus.

14. A device for testing a neutral electrode for use in electrosurgery, comprising a measuring surface which is formed by a plurality of measuring electrodes whereon the neutral electrode may be applied, wherein each measuring electrode of the measuring surface is connected to a respective equivalent resistance circuit configured to represent layers of the human skin comprising at least the hypodermis including fatty tissue, wherein each respective equivalent resistance circuit has at least two resistances, wherein each equivalent resistance circuit is in thermal contact with at least one temperature sensor, wherein the plurality of measuring electrodes are provided on a first side of a measuring circuit board which forms the measuring surface and wherein the resistances of the associated equivalent resistance circuit are arranged on a second, opposite side of the measuring circuit board, the device characterized in that the temperature sensors are arranged on an additional circuit board which is spaced from the measuring circuit board by a drilled board provided with through holes, wherein the temperature sensors face the resistances of the equivalent resistance circuits and project into the through holes of the drilled board.

15. The device according to claim 14, characterized in that the plurality of measuring electrodes are arranged in the form of a matrix on the measuring circuit board with the through holes of the drilled board being concentrically arranged with respective ones of the plurality of measuring electrodes and that the through holes are arranged concentrically with respective measuring electrodes.

16. The device according to claim 14 or 15, characterized in that the space between the resistances of the equivalent resistance circuits and the temperature sensors within the through holes is filled with a heat-conducting material.

17. The device according to claim 14 or 15, characterized in that the space between the resistances of the equivalent resistance circuits is filled with a heat-insulating material.

18. The device according to any one of the claims 14 to 15, characterized in that the resistances of the equivalent resistance circuits and the temperature sensors are formed by SMD components.

19. The device according to any one of claims 14 to 15, characterized in that the resistances of a respective one of the equivalent resistance circuits is arranged in the immediate vicinity of the associated measuring electrode on the opposite side of the measuring circuit board and are connected to the associated measuring electrode via at least one feedthrough.

* * * * *

UNITED STATES PATENT AND TRADEMARK OFFICE
CERTIFICATE OF CORRECTION

| | | |
|---|---|---|
| PATENT NO. | : 8,545,494 B2 | Page 1 of 1 |
| APPLICATION NO. | : 10/528841 | |
| DATED | : October 1, 2013 | |
| INVENTOR(S) | : Norbert Nessler | |

It is certified that error appears in the above-identified patent and that said Letters Patent is hereby corrected as shown below:

In the Specification:

Column 8, line 8, reads "(COM)"
       should read -- (CQM) --.

In the Claims:

In Claim 15:

Column 16, lines 9-11, reads "respective ones of the plurality of measuring electrodes and that the through holes are arranged concentrically with respective measuring electrodes."
    should read -- respective ones of the plurality of measuring electrodes --.

Signed and Sealed this
Third Day of December, 2013

Margaret A. Focarino
*Commissioner for Patents of the United States Patent and Trademark Office*